United States Patent [19]

Finkelstein et al.

[11] Patent Number: 4,992,459
[45] Date of Patent: Feb. 12, 1991

[54] DOPAMINE-β-HYDROXYLASE INHIBITORS

[75] Inventors: Joseph A. Finkelstein, Philadelphia, Pa.; James S. Frazee, Sewell, N.J.; Carl Kaiser, Haddon Heights, N.J.; Lawrence I. Kruse, Haddonfield, N.J.; Thomas B. Leonard, Haverford, Pa.

[73] Assignee: SmithKline Beecham Corporation, Philadelphia, Pa.

[21] Appl. No.: 167,610

[22] Filed: May 18, 1988

Related U.S. Application Data

[63] Continuation of Ser. No. 898,165, Aug. 18, 1986, abandoned, which is a continuation-in-part of Ser. No. 590,665, Mar. 19, 1984, abandoned, which is a continuation-in-part of Ser. No. 484,122, Apr. 12, 1983, abandoned.

[51] Int. Cl.$^5$ .................. A61K 31/415; C07D 233/66; C07D 233/30
[52] U.S. Cl. .................. 514/398; 548/337; 548/317
[58] Field of Search .................. 548/337, 317; 514/398

[56] References Cited

U.S. PATENT DOCUMENTS

| 3,488,423 | 1/1970 | Doebel et al. | 548/337 |
| 3,915,980 | 10/1975 | Gebert et al. | 548/337 |
| 4,340,738 | 7/1982 | Sipido | 548/337 |
| 4,487,761 | 12/1984 | Cole et al. | 548/337 |
| 4,532,331 | 7/1985 | Frazee et al. | 548/337 |
| 4,798,843 | 1/1989 | Kruse | 548/337 |

FOREIGN PATENT DOCUMENTS

| 951 | 8/1978 | European Pat. Off. | 548/337 |
| 125033 | 4/1984 | European Pat. Off. | 548/337 |
| 1155580 | 10/1966 | United Kingdom | 548/337 |
| 2096987 | 4/1981 | United Kingdom | 548/337 |

OTHER PUBLICATIONS

Iverson et al., *Acta Chem. Scand.*, 21:279-285, (1967).
Fuller et al., *Adv. Enzyme Regul.*, 15;267-281, (1976).
Runti et al., *Il. Farmaco Ed. Sc.*, 36:260-268, (1980).
Goldstein, *Pharmacol. Rev.*, 18:77-82, (1966).
Gebert et al., Chemical Abstracts, 72:39275e, (1970).
Hidaka et al., *Mol. Pharmacol.*, 9:172-177, (1973).

*Primary Examiner*—Mary C. Lee
*Assistant Examiner*—Robert C. Whittenburgh
*Attorney, Agent, or Firm*—Mary E. McCarthy; Stuart R. Suter; Edward T. Lentz

[57] ABSTRACT

Potent DBH inhibitors having the formula

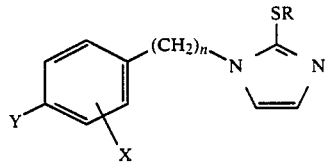

can be used to inhibit DBH activity in mammals.

44 Claims, No Drawings

DOPAMINE-β-HYDROXYLASE INHIBITORS

This is a continuation of U.S. Pat. application Ser. No. 898,165, filed Aug. 18, 1986, now abandoned which is a continuation-in-part of U.S. Pat. application Ser. No. 590,665, filed Mar. 19, 1984, now abandoned which is a continuation-in-part of U.S. Pat. application Ser. No. 484,122, filed Apr. 12, 1983 now abandoned.

FIELD OF THE INVENTION

This invention relates to inhibitors of dopamine-β-hydroxylase.

BACKGROUND OF THE INVENTION

In the catecholamine biosynthetic pathway, tyrosine is converted in three steps to norepinephrine (NE). Intermediates are dihydroxyphenylalanine (DOPA) and dopamine (DA). The latter is hydroxylated to norepinephrine by dopamine-β-hydroxylase (DBH) in the presence of oxygen and ascorbic acid.

Inhibition of catecholamine activity has been found to decrease hypertension. See, for example, Matta et al., Clin. Pharm. Ther. 14, 541 (1973), and Teresawa et al., Japan Circ. J. 35, 339 (1971). Weinshilboum, Mayo Clin. Proc. 55, 39 (1980), reviews compounds which inhibit catecholamine activity by interfering with adrenergic receptors. Alternatively, the catecholamine biosynthetic pathway can be suppressed at any of the three steps, resulting in decreased levels of NE. In addition to decreasing hypertension, inhibitors of NE synthesis are active as diuretics, natriuretics, cardiotonics and vasodilators.. Inhibition of DBH activity can have the added advantage of increasing levels of DA, which as reported by Ehrreich et al., "New Antihypertensive Drugs," Spectrum Publishing, 1976, pp. 409-432, has been found to have selective vasodilator activity at certain concentrations.

DBH inhibitors have also been shown to reduce or prevent formation of gastric ulcers in rats by Hidaka et al., "Catecholamine and Stress," edit. by Usdin et al., Permagon Press, Oxford, 1976, pp. 159-165 and by Osumi et al., Japan. J. Pharmacol. 23, 904 (1973).

A number of DBH inhibitors are known. These are generally divided into two classes, namely, metal chelating agents, which bind to copper in the enzyme, and phenethylamine analogues. Rosenberg et al., "Essays in Neurochemistry and Neuropharmacology, Vol. 4," edit. by Youdim et al., John Wiley & Sons, 1980, pp. 179-192, and Goldstein, Pharmacol. Rev. 18(1), 77 (1966), review DBH inhibitors. The former report that many of the potent DBH inhibitors have a hydrophobic side chain of size comparable to the aromatic ring of DA, leading the authors to suggest that incorporation of a terminal hydroxyl group on a 4- to 6- carbon side chain on a phenethylamine analogue might yield a potent inhibitor.

Known inhibitors include:

5-alkylpicolinic acids [See, Suda et al., Chem. Pharm. Bull. 17, 2377 (1969); Umezawa et al., Biochem. Pharmacol 19, 35 (1969); Hidaka et al., Mol. Pharmacol. 9, 172 (1973); Miyano et al., Chem. Pharm. Bull. 26, 2328 (1978); Miyano et al., Heterocycles 14, 755 (1980); Claxton et al., Eur. J. Pharmacol. 37, 179 (1976)];

BRL 8242 [See, Claxton et al., Eur. J. Pharmacol. 37, 179 (1976)];

1-alkyl-2-mercaptoimidazole [See, Hanlon et al., Life Sci. 12, 417 (1973); Fuller et al., Adv. Enzyme Regul. 15, 267 (1976)];

substituted thioureas [See, Johnson et al., J. Pharmacol. Exp. Ther. 168, 229 (1969)]; and benzyloxyamine and benzylhydrazine [See, Creveling et al., Biochim. Biophys. Acta 64, 125 (1; Creveling et al., Biochim. Bioohvs. Res. Commun. 8, 215 (1962); van der Schoot et al., J. Pharmacol. Exp. Ther. 141, 74 (1963). Bloom, Ann. N. Y. Acad. Sci. 107, 878 (1963)].

All of the above compounds except benzyloxyamine and benzylhydrazine apparently owe their inhibitory effect to metal chelating properties. Alkyl derivatives of 2-mercaptoimidazole are more potent, presumably due to non-specific interaction of the alkyl substituent with the enzyme. Benzyloxyamine and benzylhydrazine are phenethylamine derivatives which apparently act as competitive inhibitors.

In addition to the above compounds, Runti et al., Il Farmaco Ed. Sc. 36, 260 (1980), report that other fusaric acid derivatives and analogues inhibit DBH. These include phenypicdlinic acid, which is reported to have twice the inhibitory activity of fusaric acid, and 5-(4-chlorobutyl)picolinic acid, and others such as substituted amides of fusaric acid and acids and amides of 5-butyroylpicolinic acid, 5-aminopicolinic acid and 5-hydrazinopicolinic acid, and derivatives thereof.

Hidaka et al., Molecular Pharmacology, 9, 172-177 (1973) report that 5-(3,4-dibromo)butyl picolinic acid and 5-(dimethyldithiocarbamoyl)methyl picolinic acid are DBH inhibitors.

Bupicomide, 5-(n-butyl)picolinamide, is reported by Ehrreich et al., "New Antihypertensive Drugs," Spectrum Publications, 1976, pg. 409-432, to be a DBH inhibitor and to have antihypertensive activity. Friedman et al. Psychosomatic Med. 40, 107 (1978), report that patients treated with alpha-methyl-DOPA, guanethidine and reserpine, but not propanolol and diuretics, have lowered DBH levels, although the significance of the observation is uncertain.

Although there are many known inhibitors of DBH, most of these agents have not found clinical application because of non-specific, often toxic, properties they possess. Fusaric acid, for example, is hepatotoxic. See, for example, Teresawa et al., Japan. Cir. J. 35, 339 (1971) and references cited therein. Presumably, the picolinic acid structure interacts with a number of metalloproteins and enzymes in non-specific fashion to produce observed side effects.

In U.K. specification 1,555,580 are disclosed compounds having the formula:

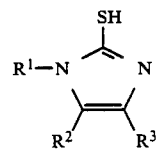

wherein $R^2$ and $R^3$ can be H and $R^1$ can be substituted phenyl. The compounds are said to have analgesic, antiinflammatory and antipyretic properties. Gebert et al., U.S Patent 3,915,980, disclose such compounds wherein $R^1$ can be phenyl or phen($C_{1-3}$) alkyl, as intermediates to imidazolyl-2-thioalkanoic acid esters.

Iverson, Acta Chem. Scand. 21, 279 (1967) reports a compound having the formula:

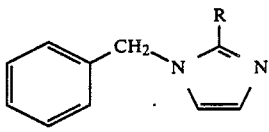

herein R can be —CO₂H or —CH₂NCH₆H₅, but does not report a pharmaceutical use for the compound.

In European Patent Application No. 125,033 (published Nov. 14, 1984) a series of 1-phenyl and 1-phenylalkylimidazole compounds having a mercapto or alkylthio group in the 2-position are disclosed. These compounds are described as having DBH inhibiting activity.

U.S. Pat. No. 4,532,331 describes various 1-benzyl-2-aminomethylimidazole derivatives that inhibit DBH activity and includes pharmaceutical compositions containing these derivatives and methods of using these derivatives to inhibit DBH activity.

SUMMARY OF THE INVENTION

The invention resides in the discovery that DBH is inhibited by a compound having a mercaptoimidazole moiety and a phenethylamine analogue moiety. More particularly, the invention is selected novel compounds having the formula:

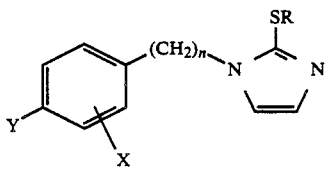

wherein:

X is —H, —OH, halogen, $C_{1-4}$ alkyl, —CN, —NO₂, —SO₂NH₂, —CO₂H, —CONH₂, —CHO, —CH₂OH, -CF₃, $C_{1-4}$ alkoxy, —SO₂$C_{1-4}$ alkyl, —SO₂$C_{1-4}$ fluoroalkyl, —CO₂$C_{1-4}$ alkyl or any accessible combination thereof up to four substituents;

Y is —H, —OH, $C_{1-4}$ alkoxy, halogen, $C_{1-4}$ alkyl, —CN, —NO₂—SO₂CONH₂, -CO2H, —CHO, —CH₂OH, —CF₃, —SO₂$C_{1-4}$ alkyl, —SO₂$C_{1-4}$ fluoroalkyl, or —CO₂$C_{1-4}$ alkyl;

R is —H or $C_{1-4}$ alkyl; and n is 0–4, or a hydrate or, when R is $C_{1-4}$ alkyl, a pharmaceutically acceptable acid addition salt thereof, provided that when n is 0, Y is —OH and when n is 1–3, at least one of Y and X is not —H. As used herein, "accessible combination thereof" means any other stable combination of substituents available by chemical synthesis.

In preferred compounds of the invention, Y is —OHH or —OCH₃; R is —H; n is 1 or 3; and X is —H, —OH or halogen (in particular, 3,5-dichloro, 3,5-difluoro, 3-chloro, or 3-fluoro) or Y is —H; R is —H; n is 1 or 3 and X is halogen (in particular, 3,5-dichloro, 3,5-difluoro, 3-chloro, or 3-fluoro). In the most preferred compound of the invention, Y is —H, X is 3,5-difluoro, R is —H and n is 1.

The invention is also a method of inhibiting DBH activity in mammals which comprises administering internally to a subject an effective amount of a compound having the formula:

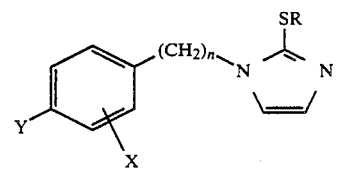

wherein:

X is —H, —OH, halogen, $C_{1-4}$ alkyl, —CN, —NO₂, —SO₂—CONH₂, —CHO, —CH₂, OH, —CF₃, $C_{1-4}$ alkoxy, —SO₂$C_{1-4}$ alkyl, —SO₂$C_{1-4}$ fluoroalkyl, —CO₂$C_{1-4}$ alkyl or any accessible combination thereof up to four substituents;

Y is —H, —OH, $C_{1-4}$ alkoxy, halogen, $C_{1-4}$ alkyl, —CN, —NO₂, —SO₂NH₂, —CO₂H, —CONH₂, —CHO, —CH₂OH, —CF₃, —SO₂$C_{1-4}$ alkyl, —SO₂$C_{1-4}$ fluoroalkyl, or —CO₂$C_{1-4}$ alkyl;

R is —H or $C_{1-4}$ alkyl; and n is 0–4, or a hydrate or, when R is $C_{1-4}$ alkyl, a pharmaceutically acceptable acid addition salt thereof.

Compounds found to be especially potent, and therefore preferred in the method of invention, are those in which Y is —OH or OCH₃; R is —H; n is 1 or 3; and X is —H, —OH or halogen (in particular, 3,5-dichloro 3,5-difluoro, 3-chloro or 3-fluoro) or Y is —H; R is —H; n is 1 or 3 and X is halogen (in particular, 3,5-dichloro, 3,5-difluoro, 3-chloro, or 3-fluoro). In the most preferred method of the invention, Y is —H; X is 3,5-difluoro, R is —H and n is 1.

It is intended that the above formulae include the tautomer of the compounds wherein R is —H, that is, the compounds having the above formulae wherein the imidazole moiety has the formula:

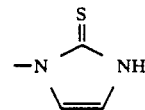

The above formulae also include hydrates of the compounds and pharmaceutically acceptable acid addition salts of the compounds wherein R is $C_{1-4}$ alkyl. The invention also includes pharmaceutical compositions comprising the compounds having the above formulae, provided that when n is 0, Y is —OH, and pharmaceutical carriers.

The invention is also intermediates to the compound of the invention, said intermediates having the formula:

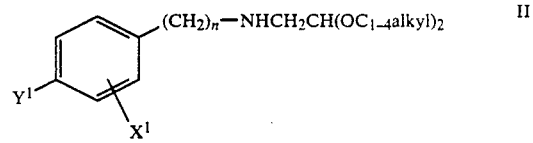

wherein $Y^1$ and $X^1$ are the same as Y and X but are not —OH and n is 0–4 and

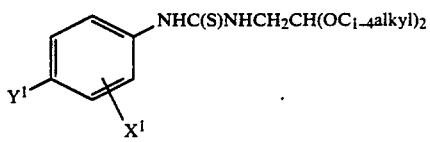

wherein $X^1$ is the same as X but is not —OH, $Y^1$ is $C_{1-4}$ alkoxy, preferably —OCH3 and n is 0.

The invention is also a process for preparing the compound of the invention which comprises contacting and reacting compound II, above, with acidic thiocyanate and such process which comprises contacting and reacting compound II A, above, with an acid to cyclize the compound. In both processes, when $Y^1$ and/or $X^1$ are $C_{1-4}$ alkoxy, Y and/or X are optionally deprotected to prepare the compound wherein Y and/or X are —OH.

DETAILED DESCRIPTION OF THE INVENTION

The compounds of the present invention contain weak metal-chelating functional groups derived from N-methyl-2-mercaptoimidazole which is known to be a weak DBH inhibitor. The compounds of the invention also contain phenyl moieties as do phenethylamine analogue inhibitors such as benzyloxyamine, benzylhydrazine, tryptamine and serotonin.

The compounds of the invention and the compounds used in the method of the invention can be prepared from corresponding starting benzyl or phenyl compounds such as benzaldehydes, which are known and described in published references or are readily accessible, by known techniques such as illustrated in Scheme I, below, wherein $X^1$ and $Y^1$ are X and Y, respectively, except that when Y is —OH, $Y^1$ is $C_{1-4}$ alkoxy, preferably —OCH3, and when X is —OH, $X^1$ is $C_{1-4}$ alkoxy, preferably —OCH3. As illustrated, n is one, although n can be 0-4. Scheme I illustrates reductive amination of benzaldehydes (I) with an aminoacetaldehyde acetal followed by reduction by, for example, catalytic hydrogenation or treatment with a reducing agent such as NaBH4, LiAlH4 or AlH3, to provide intermediate substituted benzylamines (II). Upon reaction with acidic thiocyanante, the intermediates (II) yield mercaptoimidazole products (III). The mercaptoimidazole products can be prepared from other than benzaldehydes, as illustrated in Examples 1 and 4, below.

Scheme I

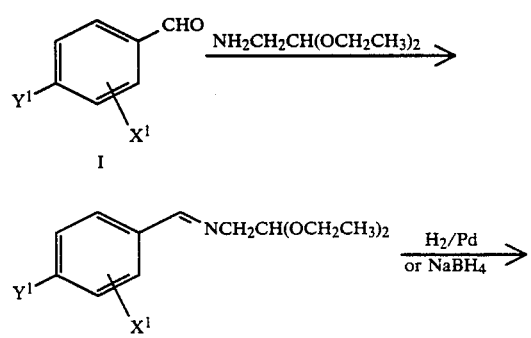

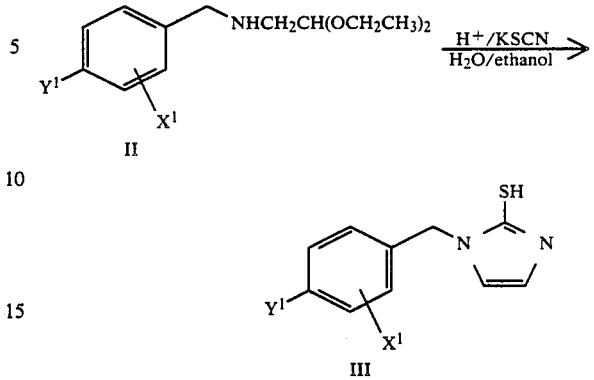

The 1-phenyl substituted 2-mercaptoimidazoles (n is 0) are preferably prepared by reaction of an appropriately substituted phenyl isothiocyanate with an aminoacetaldehyde acetal followed by strong acid catalyzed cyclization, as illustrated in Example 1, below.

The compounds wherein n is 2, 3 or 4 are preferably prepared as illustrated in Example 4 and in Examples 23 and 24, below. Coupling of substituted phenylalkanoic acids as the acid halides, preferably chlorides, with aminoacetaldehyde acetals and subsequent reduction provided such intermediate substituted phenylalkylamines.

$Y^1$ in Scheme I is the same as Y except that when Y is —OH, $Y^1$ is $C_{1-4}$ alkoxy, preferably —OCH3, optional deprotection of the 4-alkoxy group with, for example, BBr3 or HBr, or nucleophilic aromatic substitution with dilute hydroxide, provides the phenol (Y is —OH). $X^1$ may be one or more substituents at the 2-, 3-, 5- or 6- positions, provided the combination of substituents is accessible, that is, does not result insignificant instability due to steric hindrance. When Xl is $C_{1-4}$ alkoxy, preferably —OCH3, it can be deprotected as described above for $Y^1$ The compounds in which R is $C_{1-4}$ alkyl are preferably prepared by allowing the deprotection with, for example, BBr3, in an alkanol to proceed to formation of an alkyl bromide which alkylates the mercapto group as illustrated in Example 6, below. Alternatively, a solution or suspension of an appropriately substituted mercaptoimidazole in an inert solvent, for example, methanol, tetrahydrofuran or aqueous dimethylformamide, can be reacted with an alkylating agent, for example, alkyl iodide, bromide or tosylate. Methyl iodide is preferred in this alternative procedure.

The pharmaceutically acceptable acid addition salts of the compounds wherein R is $C_{1-4}$ alkyl are formed with strong or moderately strong organic or inorganic acids by methods known to the art. For example, the base is reacted with an inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Exemplary of the salts which are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

The compounds of the invention, because they can be used to inhibit DBH activity, have therapeutic value as diuretic, natriuretic, cardiotonic, antihypertensive and vasodilator agents, as well as antiulcerogenic and anti-parkinson disease agents.

Compounds of the invention and other compounds useful in the method of the invention were screened for in vitro DBH inhibition by a standard procedure for assaying conversion of tyramine to octopamine in the presence of DBH. Octopamine was assayed following sodium periodate oxidation to p-hydroxybenzaldehyde by measuring spectrophotometric absorbance at 330 nm. Results are given in Table I, below. Inhibition is given in molar concentration of compound at which DBH activity was halved ($IC_{50}$ Melting points (mp) are given in ° C. By this procedure fusaric acid was found to have an $IC_{50}$ of about $8 \times 10^{-7}$.

TABLE I

| n | X | Y | R | mp | $IC_{50}$ |
|---|---|---|---|---|---|
| 1 | 3-Br | OH | H | 181 | $1.2 \times 10^{-5}$ |
| 1 | 3-F | OH | H | 172 | $1.4 \times 10^{-6}$ |
| 1 | 3-F | $OCH_3$ | H | 156–157 | $10^{-4}$ (67% inhibition) |
| 1 | 3-OH | H | H | 167 | $1.5 \times 10^{-4}$ |
| 1 | 2-OH | H | H | 158 | $5.8 \times 10^{-4}$ |
| 1 | 3-$CH_3$ | OH | H | 214–216 | $4.8 \times 10^{-5}$ |
| 1 | 2-$OCH_3$ | H | H | 159 | $10^{-4}$ (68% inhibition) |
| 1 | 3-$OCH_3$ | H | H | 118–121 | $10^{-4}$ (72% inhibition) |
| 4 | H | OH | H | 132–134 | $10^{-4}$ (12% inhibition) |
| 3 | H | OH | $CH_3$ | 140–142 | $7.9 \times 10^{-5}$ |
| 1 | 3,5-$Cl_2$ | OH | H | 220–222 (dec) | $7.4 \times 10^{-7}$ |
| 1 | 3-$NO_2$ | OH | H | 224–227 | $2.0 \times 10^{-5}$ |
| 1 | 2,6-$Cl_2$ | OH | H | >235 (dec) | $7.5 \times 10^{-5}$ |
| 1 | 3,5-$F_2$ | OH | H | 213–215 | $7.4 \times 10^{-8}$ |
| 1 | 3,5-$F_2$ | $OCH_3$ | H | 160–161 | $3.6 \times 10^{-5}$ |
| 1 | 3-$CF_3$ | OH | H | 220 (dec) | $1.2 \times 10^{-4}$ |
| 1 | 2,3,5,6-$F_4$ | OH | H | 203–5 | $6.2 \times 10^{-5}$ |
| 1 | H | H | H | 144–5 | $1.1 \times 10^{-5}$ |
| 2 | H | OH | H | 181–184 | $1.8 \times 10^{-5}$ |
| 0 | H | H | H | 180–182 | $1.0 \times 10^{-4}$ |
| 1 | H | OH | H | 188–190 | $2.3 \times 10^{-6}$ |
| 3 | H | OH | H | 183–185 | $2.0 \times 10^{-6}$ |
| 1 | 3-OH | OH | H | 209–212 | $4.0 \times 10^{-6}$ |
| 0 | H | OH | H | 260–264 | $3.2 \times 10^{-4}$ |
| 1 | 3-Cl | OH | H | 186–190 | $2 \times 10^{-6}$ |
| 1 | 2,6-$Cl_2$ | H | H | 242–243 | $10^{-4}$ (7% inhibition) |
| 1 | 2-Cl | H | H | 206–207 | $10^{-4}$ (14% inhbition) |
| 1 | 2,5-$Cl_2$ | H | H | 265 (dec) | $9.7 \times 10^{-5}$ |
| 1 | 4-Cl | H | H | 187–189 | $9.6 \times 10^{-5}$ |
| 1 | 2,3-$Cl_2$ | H | H | 195–197 | $5.2 \times 10^{-5}$ |
| 1 | H | F | H | 167–169 | $4.7 \times 10^{-5}$ |
| 1 | 3,4-$Cl_2$ | H | H | 178–181 | $2.8 \times 10^{-5}$ |
| 1 | 2,4-$Cl_2$ | H | H | 185–187 | $1.7 \times 10^{-5}$ |
| 1 | 3-Cl | H | H | 129–131 | $1.2 \times 10^{-5}$ |
| 1 | 3,5-$Cl_2$ | H | H | 209–211 | $2.4 \times 10^{-6}$ |
| 1 | 2,4,6-$Cl_3$ | H | H | 240–244 | $1.0 \times 10^{-4}$ |
| 1 | 3-F | H | H | 113–114 | $5.6 \times 10^{-6}$ |
| 1 | 3,5-$F_2$ | H | H | 140–141 | $1.2 \times 10^{-6}$ |
| 3 | 3,5-$Cl_2$ | H | H | 98–99 | $2.0 \times 10^{-6}$ |
| 3 | 3,5-$F_2$ | H | H | 131–132 | $4.7 \times 10^{-6}$ |

The above results illustrate that compounds of the invention and other compounds useful in the method of the invention inhibit DBH activity.

The following procedure was used to screen compounds of the invention for activity in vivo. Male Okamoto-Aoki strain spontaneously hypertensive rats (SHR), 270–340 g, aged 16–20 weeks, were used for testing. The afternoon before testing, the animals were fasted and the following morning the first dose .fo the test compound was administered, p.o., along with a 25 ml/kg, load of normal saline. The animals were then placed in metabolism cages, three per cage, and urine was collected for three h4 and subsequently analyzed for sodium, potassium, and creatinine. Indirect systolic blood pressure and heart rate were measured via a tail-cuff method and, within 24 hr of the first dose, the animals received an identical second dose of the test compound. Two hr after the second dose, the systolic blood pressure and heart rate were again determined. Drugs were administered intraperitoneally as a solution or suspension in 0.9% NaCl with 0.02% ascorbic acid. The dose volume was 5 ml.

Averaged results of the in vivo screens are given in Table II. In all compounds tested, R is —H and Y is —OH. Except where otherwise indicated, the concentration was 50 mg/kg. Averaged results with control animals are listed in parentheses below results of treated animals.

TABLE II

| Compound | | No. of Animals | Electrolytes Execrated (mEq/rat) | | Urine Vol. (ml/rat) | $Na^+/K^+$ Ratio | Systolic Blood Pressure (mmHg) | | Heart Rate (beats/min) | |
|---|---|---|---|---|---|---|---|---|---|---|
| x | n | | $Na^+$ | $K^+$ | | | First Dose | Second Dose | First Dose | Second Dose |
| 3-Cl | 1 | 3 | 280.33 | 182.22 | 8 | 1.538 | 173 | 180 | 400 | 440 |
| | | (3) | (381.56) | (133.79) | (8) | (2.852) | (174) | (170) | (440) | (460) |
| 3-F | 1 | 3 | 162.07 | 134.81 | 3 | 1.202 | 177 | 191 | 460 | 420 |
| | | (3) | (214.16) | (198.80) | (6) | (1.077) | (188) | (189) | (460) | (440) |
| H | 3(1) | 3 | 185.81 | 160.59 | 5 | 1.157 | 181 | 185 | 440 | 440 |
| H | 3(2) | 3 | 339.19 | 231.19 | 8 | 1.467 | 187 | 180 | 380 | 440 |
| | | (3) | (390.84) | (231.19) | (8) | (1.691) | (193) | (192) | (480) | (460) |
| H | 3 | 3 | 334.84 | 104.72 | 8 | 3.197 | 181 | 163 | 460 | 460 |
| | | (3) | (183.41) | (91.11) | (4) | (2.013) | (183) | (180) | (460) | (460) |
| 3,5-$Cl_2$ | 1 | 3 | 541.03 | 293.07 | 13.0 | 1.846 | 167 | 160 | 440 | 500 |
| | | (3) | (333.42) | (153.17) | (6.5) | (2.177) | (167) | (176) | (400) | (460) |
| 3-OH | 1 | 3 | 149.10 | 174.26 | 4 | 0.856 | 185 | 173 | 460 | 480 |
| | | (3) | (161.19) | (154.61) | (4) | (1.043) | (180) | (185) | (480) | (400) |
| 3-OH | 1(2) | 3 | 383.61 | 205.29 | 10 | 1.869 | 173 | 178 | 440 | 440 |
| | | (3) | (395.72) | (164.23) | (8) | (2.409) | (171) | (199) | (420) | (480) |
| H | 1 | 3 | 369.40 | 251.79 | 11 | 1.467 | 181 | 183 | 400 | 440 |
| | 1(1) | 3 | 495.00 | 229.27 | 11 | 2.159 | 193 | 182 | 480 | 480 |
| | | (3) | (344.55) | (137.84) | (9) | (2.500) | (171) | (183) | (380) | (440) |
| 3,5-$Cl_2$* | 3 | 3 | 103.46 | 53.34 | 1 | 1.940 | 147 | 153 | 320 | 400 |
| | | (3) | (146.06) | (20.11) | (2) | (7.264) | (179) | (186) | (420) | (460) |

TABLE II-continued

| Compound x | No. of Animals | Electrolytes Execrated (mEq/rat) | | Urine Vol. (ml/rat) | Na+/K+ Ratio | Systolic Blood Pressure (mmHg) | | Heart Rate (beats/min) | |
|---|---|---|---|---|---|---|---|---|---|
| | | Na+ | K+ | | | First Dose | Second Dose | First Dose | Second Dose |
| 3,5-Cl$_2$* | 3 | 86.67 | 54.32 | 3.5 | 1.596 | 159 | 141 | 360 | 360 |
| | (3) | 128.60 | 77.25 | 3 | 1.665 | 172 | 182 | 400 | 480 |

[1] dose concentration = 12.5 mg/kg.
[2] dose concentration = 25.0 mg/kg.
*Y is -H.

It is apparent from Table II that the compounds tested have significant diuretic and/or cardiotonic activity. The compounds in which X is 3,5-dichloro showed significant natriuretic activity as well as diuretic, antihypertensive and cardiotonic activity. Compounds having diuretic activity are known to be useful as antihypertensives.

In additional experiments carried out substantially by the above procedure, the compound in which X is 3,5—F$_2$, Y is —H, R is —H and n is 1 (50 mg/kg) was found to have an especially pronounced effect on urine excretion, increasing urine volume about four fold over controls. Heart rate was generally decreased by administration of the compound.

Various compounds of the invention, as well as various known DBH inhibitors, were tested for their effects on peripheral dopamine and norepinephrine levels substantially by the procedure of DaPrada and Zürcher, *Life Sci.* 19, 1161 (1976). Spontaneously hypertensive rats were dosed twice, the second dose being about 18 hr after the first, and were sacrificed about 2 hr after the second dose. Averaged results, expressed in micrograms of DA per gram of tissue, are given in Table III and in Table III A, which follow. In Table III, R=—H, Y=—OH and n=1; in Table III A, R=—H, Y=—H and n=1; in Table III B, R=—H, Y=—OCH$_3$, and n=1.

TABLE III

| Compound | No. of Animals | DA ($\mu$g/g) | | DA/NE Ratio | |
|---|---|---|---|---|---|
| Control (H$_2$O) | 11 | .260 | .019 | .040 | .002 |
| Fusaric Acid | 11 | .520 | .053[1] | .100 | .007[1] |
| Control | 3 | .219 | .044 | .035 | .002 |
| Hydralazine | | | | | |
| (25 mg/kg) | 3 | .417 | .026[2] | .078 | .015[2] |
| (50 mg/kg) | 1 | .835 | .127 | .098 | .018 |
| Control | 1 | .299 | .038 | .039 | .004 |
| X = 3-F | 1 | .476 | .023[3] | .064 | .004[2] |
| (50 mg/kg) | | | | | |
| Control | 1 | .261 | .046 | .041 | .007 |
| X = 3-F | | | | | |
| (50 mg/kg) | 1 | .430 | .027[3] | .082 | .005[3] |
| (100 mg/kg) | 1 | .619 | .071[3] | .099 | .003[1] |
| Control | 1 | .273 | .019 | .040 | .002 |
| X = 3,5-Cl$_2$ | 1 | .241 | .031[3] | .045 | .006[3] |
| (50 mg/kg) | | | | | |
| Control | 1 | .242 | .014 | .030 | .002 |
| (cold-stressed) | | | | | |
| X = 3,5-Cl$_2$ | 1 | .313 | .019[2] | .038 | .003[2] |
| (50 mg/kg) | | | | | |
| (cold-stressed) | | | | | |
| Control | 5 | .270 | .025 | .0307 | .0019 |
| Fusaric Acid | 5 | .675 | .030[1] | .0871 | .0047[1] |
| (50 mg/kg) | | | | | |
| X = 3,5-F$_2$ | 5 | .708 | .068[1] | .0824 | .0128[2] |
| (50 mg/kg) | | | | | |

[1] P < 0.001
[2] P < 0.05
[3] P < 0.01

TABLE IIIA

| Compound | No. of Animals | DA ($\mu$g/g) | DA/NE Ratio |
|---|---|---|---|
| Control | 4 | .319 ± .104 | .042 ± .012 |
| Fusaric Acid | 5 | .642 ± .114 | .1240 ± .0140[1] |
| X = 3-F | 5 | 1.096 ± .080 | .1946 ± .0112[1] |
| n = 1 | | | |
| (50 mg/kg) | | | |
| X = 3,5-F$_2$ | 5 | 2.109 ± .123 | .4485 ± .0532[1] |
| (50 mg/kg) | | | |
| Control | 5 | .250 ± .014 | .037 ± .003 |
| X = 3,5-Cl$_2$ | 5 | .670 ± .065 | .110 ± .008[1] |
| (50 mg/kg) | | | |
| Control | 5 | .308 ± .023 | .045 ± .004 |
| X = 3,5-Cl$_2$ | 5 | .688 ± .020 | .103 ± .002[1] |
| (50 mg/kg) | | | |

[1] P < 0.001

TABLE IIIB

| Compound | No. of Animals | DA ($\mu$g/g) | DA/NE Ratio |
|---|---|---|---|
| Control | 6 | .318 ± .008 | .0393 |
| X = 3-F | 6 | 1.397 ± .111 | .239[1] |
| X = 3,5-F$_2$ | 6 | 1.178 ± .087 | .204[1] |

[1] P 0.001

The above results illustrate that the compounds of the invention inhibit DBH activity in mammals when administered internally in effective amounts. The compound of the invention in which X is —H, Y is —OH, R is —H and n is 3 was also tested in one rat. The results did not indicate significant inhibition of DBH activity. Nevertheless, because only a single experiment was run, because other compounds of the invention show such activity, and because the compound has a low in vitro IC$_{50}$ (See Table I), the compound is believed to be useful in inhibiting DBH activity in mammals.

The compounds in which Y is —H and X is halogen, especially difluoro and dichloro, show high in vivo activity, as shown in Table IIIA. The compound in which X is 3,5 difluoro, Y is —H, R is —H and n is 1 (IC$_{50}$=1.2 ×10$^{-6}$) showed an especially pronounced effect on the DA/NE ratio in vivo. Additionally, although relatively weak in vitro DBH inhibitors, as indicated by the data in Table IIIB, compounds in which Y is —OCH$_3$, n is 1, and X is 3—F or 3,5—F$_2$ proved very potent DBH inhibitors in vivo.

In a study on the effect on blood pressure in spontaneously hypertensive rats of daily doses of compounds of the invention (50 mg/kg, i.p.), the compound in which X is 3,5-dichloro, Y is —H, R is —H and n is 1 exhibited a cumulative effect, that is, blood pressure continued to decrease on each day of the four day study period.

Another study was conducted to compare the effects on blood pressure of compounds wherein Y is —OH, X is 3—F or 3,5—F$_2$ and n is 1 to their Y is —OCH$_3$ analogues. The maximum blood pressure reduction observed after administration of the hydroxy compound in which X is 3—F was 18%, whereas one-half the dose of its methoxy analogue produced a 35% blood pressure reduction. Also, equivalent doses of the compound in which Y is —OH, X is 3,5—F$_2$, and n is 1 and its Y is —OCH3 analogue produced, respectively, 20% and 35% blood pressure reductions.

The compounds can be incorporated into convenient dosage unit forms such as capsules, tablets or injectable preparations. Pharmaceutical carriers which can be employed can be solid or liquid. Solid carriers include, among others, lactose, terra alba, sucrose, talc, gelatin, agar, pectin, acacia, magnesium stearate, and stearic acid Liquid carriers include, among others, syrup, peanut oil, olive oil and water. Similarly, the carrier or diluent may include any delayed release material, such as glyceryl monostearate or glyceryl distearate, alone or with a wax. The amount of solid carrier will vary widely but, preferably, will be from about 25 mg to about 1 g per dosage unit. If a liquid carrier is used, the preparation will be in the form of a syrup, emulsion, soft gelatin capsule, sterile injectable liquid such as an ampule, or an aqueous or nonaqueous liquid suspension.

The pharmaceutical preparations are made following conventional techniques of a pharmaceutical chemist involving mixing, granulating and compressing, when necessary, for tablet forms, or mixing, filling and dissolving the ingredients, as appropriate, to give the desired oral or parenteral end products.

Doses of the present compounds in a pharmaceutical dosage unit will be an effective amount, that is, a nontoxic quantity selected from the range of 0.1–1,000 mg/kg of active compound, preferably 10–100 mg/kg. The selected dose is administered to a patient in need of treatment from 1–5 times daily, orally, rectally, by injection or by infusion. Parenteral administration, which uses a low dose, is preferred. However, oral administration, at a higher dose, can also be used when safe and convenient for the patient. Use of lowest effective doses is recommended because toxicity has been associated with sulfur-containing compounds.

The following examples are illustrative df preparation of compounds of the invention or intermediates therefor. The starting compounds are commercially available or are prepared by known techniques. The Examples are not intended to limit the scope of the invention as defined herein above and as claimed below. The compounds listed in Tables I, II and III, above, were prepared substantially by the illustrated procedures. All temperatures and melting points (mp) are in degrees Celsius (° C).

EXAMPLE 1

1-(4-Methoxyphenyl)-2-mercaptoimidazole

A solution of 10 g (.06 mole) of p-methoxyphenyl isothiocyanate in 100 ml of CHCl$_3$ was treated with 6.3 g (.06 mole) of aminoacetaldehyde dimethyl acetal. The solvent was evaporated and the residue was recrystallized from ethanol to yield N-(p-methoxyphenyl)-N'-($\beta$,$\beta$-dimethoxyethyl)thiourea, 9.2 g (57%). A suspension of this thiourea in a solution of 5 ml of concentrated H$_2$SO$_4$ and 20 ml of H$_2$O was refluxed for 3 hours. The mixture was cooled and a solid was filtered, washed with H$_2$O and dried. Recrystallization from ethanol gave 1-(4-methoxyphenyl)-2-mercaptomidazole, 4.9 g (70%), mp 215–7°. The compound can be deprotected, for example, as illustrated in Example 5 and 6, below, to prepare the phenol, Y is —OH.

EXAMPLE 2

1-(4-Methoxybenzyl)-2-mercaptoimidazole

A mixture of 13.6 g (0.1 mole) of anisaldehyde, 3.3 g (0.1 mole) of aminoacetaldehyde diethyl acetal and ml of CH$_3$OH was heated at 95° for 10 minutes. A residue was dissolved in 150 ml of ethanol and hydrogenated over 10% Pd on carbon at 50 psi (0.34 MPa) until H$_2$ uptake was complete. The catalyst was filtered and the filtrate was treated with 10.4 g (0.107 mole) of KSCN, 0 ml of 3N HCl and 40 ml of H$_2$O. The mixture was refluxed, letting the solvent evaporate until the volume of the reaction mixture was 100 ml. After 45 minutes, the mixture was cooled, and a solid was filtered, washed with H$_2$O and dried. Recrystallization from ethanol gave (1-(4-methoxybenzyl)-2-mercaptoimidazole, 15.0 g (68%), mp 140–142°.

EXAMPLE 3

1-(3-Bromo-4-methoxybenzyl)-2-mercaptoimidazole

A solution of 10.75 g (.05 mole) of 3-bromo-4methoxybenzaldehyde and 6.65 g (.05 mole) of aminoacetaldehyde diethyl acetal in 25 ml of ethanol was refluxed for 30 minutes. The solvent was evaporated and the residue was dissolved in CH$_2$Cl$_2$. The CH$_2$Cl$_2$ solution of the Schiff base was washed with saturated aqueous NaCl, dried (K$_2$CO$_3$) and filtered, and the solvent was evaporated. Residual Schiff base was dissolved in 100 ml of methanol, cooled to 5°, and treated with 5.0 g of NaBH$_4$. The reaction mixture was allowed to warm to 22° and, after 4 hr, the solvent was evaporated. The residue was taken up in diethyl ether, washed with H$_2$O, dried (MgS$_{SO4}$) and filtered, and the solvent was evaporated. A solution of the residue in CHC13, upon treatment with ethereal HCl, gave, on standing, crystals of N-(3-bromo-4-methoxybenzyl)aminoacetaldehyde diethylacetal hydrochloride, 10.75 g (58%), mp 112–120°.

A solution of 10.74 g (.029 mole) of N-(3-bromo4-methoxybenzyl)aminoacetaldehyde diethyl acetal hydrochloride and 3.37 g (0.35 mole) of KSCN in 50 ml of H20, 50 ml of ethanol and 5 ml of 3N HCl was refluxed for 4.5 hours. One hundred ml of H$_2$O was added and the mixture was cooled. A solid was filtered, washed with H$_2$O and dried. Recrystallization from ethanol gave 1-(3-bromo-4-methoxybenzyl)-2-mercaptoimidazole, 6.3 g (72%), mp 188°.

EXAMPLE 4

1-[3-(4-Methoxyphenyl)-propyl]-2-mercaptoimidazole

A solution of 12.5 g (.07 mole) of p-methoxyphenylpropionic acid in 100 ml of CH$_2$Cl$_2$ and one drop of pyridine was treated with 9.8 g (.077 mole) of oxalyl chloride. After 2.5 hours, the solvents were thoroughly evaporated to give the acid chloride as an oil. A solution of the acid chloride in 100 ml of CH$_2$Cl$_2$ was slowly added to a cold (0°) solution of 14.7 g (0.14 mole) of aminoacetaldehyde dimethyl acetal in 300 ml of CH$_2$Cl$_2$ at a rate such that the temperature stayed below 20°. After 1 hr, the reaction mixture was poured into H20, and the CH$_2$C12 layer was separated and washed with aqueous Na$_2$CO$_3$, 0.5N HCl and H$_2$O. Following drying and evaporation of the solvent, N-($\beta$, $\beta$B-dimethoxyethyl)-p-methoxyphenylpropionamide was obtained as a solid, 10.3 g (55%). A solution of this amide in 300 ml of diethyl ether was slowly added to a slurry of 4.0 g of LiAlH$_4$ in 400 ml of diethyl ether and 350 ml of tetrahydrofuran (THF). After 3.5 hours at 22°, excess LiAlH$_4$ was cautiously destroyed, the reaction mixture was filtered and the filtrate was evaporated. The residue was dissolved in 100 ml of 0.15N HCl, washed with diethyl ether, basified with NaHCO$_3$ and extracted with diethyl ether. The extracts were dried (MgSO$_4$) and the solvent was evaporated to give N-[3-(4-methoxyphenyl)propyl] aminoacetaldehyde dimethyl acetal, 4.6 g (52%), as an unstable oil.

A solution of 3.62 g (.014 mole) of N-[3-(4-methoxyphenyl)propyl]aminoacetaldehyde dimethyl acetal and 1.4 g (.0144 mole) of KSCN in 20 ml of ethanol, 5 ml of H$_2$O and 2 ml of concentrated HCl was refluxed for five hours. Fifty ml of H$_2$O was added, the mixture was cooled and a solid was filtered, washed with H$_2$O and dried. Recrystallization from ethanol gave 1-[3-(4-methoxyphenyl)propyl]-2-mercaptoimidazole, 2.4 g (69%), mp 108–109°.

Example 5

1-(3—Fluoro-4-methoxybenzyl)-2-mercaptoimidazole

3—Fluoro-4-methoxybenzaldehyde (5.0 g, 0.0324 mole) was added to aminoacetaldehyde dimethyl acetal (3.53 ml, 0.0324 mole) and the mixture was heated at 100° C. for 2 hours. The reaction mixture was cooled in ice, diluted with ethyl alcohol (50 ml) and sodium borohydride (1.23 g, 0.0324 mole) was added and the mixture was stirred overnight at 25° C. The solvent was removed under reduced pressure and the residue was dissolved in ethyl acetate and the solution was washed with water and brine and then dried with sodium sulfate. The mixture was filtered and the solvent removed under reduced pressure to give N-(3-fluoro-4-methoxybenzyl)-aminoacetaldehyde dimethyl acetal as an oil (6.68 g, 85%).

To a solution of 1-(3-fluoro-4-methoxybenzyl-)aminoacetaldehyde dimethyl acetal (6.68 g, 0.0275 mole) in ethyl alcohol (40 ml) was added potassium thiocyanate (2.94 g, 0.0302 mole) in water (65 ml) followed by 12 N hydrochloric acid (6 ml) and the reaction mixture was heated under reflux for 3 hours. The solvent was partially removed under reduced pressure and the mixture was cooled in ice and the product filtered. The product was recrystallized from ethyl alcohol to give 1-(3-fluoro4-methoxybenzyl)-2-mercaptoimidazole as a solid melting at 156–157° (3.98 g, 61%).

Example 6

1-(3,5-Difluoro-4-methoxybenzyl)-2-mercaptoimidazole

A mixture of 3,5-difluoro-4-methoxybenzonitrile (3.50 g, 0.0207 mole) and Raney catalyst powder (3.5 g) in 90% formic acid (35 ml) was stirred and heated under reflux for 2.5 hours and the catalyst was filtered and washed with hot water and hexane. The hexane layer was separated and the aqueous solution was extracted an additional three times with hexane. The combined hexane extracts were washed with water and brine, dried and the solvent was removed to give 3,5-difluoro-4-methoxybenzaldehyde as an oil (3.38 g, 95%).

3,5-Difluoro-4-methoxybenzaldehyde (3.38 g, 0.0196 mole) was added to aminoacetaldehyde dimethyl acetal (2.14 ml, 0.0196 mole) and the mixture was heated at 100° C. for 2 hours. The reaction mixture was cooled in ice, diluted with ethyl alcohol (35 ml), and sodium borohydride (0.743 g., 0.0196 mole) was added and the mixture was stirred overnight at 25° C. The solvent was removed under reduced pressure, the residue was dissolved in ethyl acetate, and the solution was washed with water and brine and then dried with sodium sulfate. The mixture was filtered, and the solvent removed under reduced pressure to give N-(3,5-difluoro-4-methoxybenzyl)-aminoacetaldehyde dimethyl acetal as an oil (4.94 g, 96%).

To a solution of N-(3,5-difluoro-4-methoxybenzyl)-aminoacetaldehyde dimethyl acetal (4.94 g, 0.0189 mole) in ethyl alcohol (30 ml) was added potassium thiocyanate (2.10 g, 0.0216 mole) in water (48 ml) followed by 12 N hydrochloric acid (4 ml), and the reaction mixture was heated under reflux for 3.5 hours. The solvent was partially removed under reduced pressure, the mixture was cooled in ice, and the product was filtered. The product was recrystallized from ethyl alcohol - hexane to give 1-(3,5-difluoro-4-methoxybenzyl)-2-mercaptoimidazole as a solid melting at 160–161° (2.22 g, 46%).

EXAMPLE 7

1-[3-(4—Hydroxyphenyl)propyl]-2-mercaptoimidazole

A solution of 1.75 g (0.007 mole) of 1-[3-(4methoxyphenyl)propyl]-2-mercaptoimidazole in 60 ml of CH$_2$Cl$_2$ was deprotected by treatment with a solution of 7.0 g (0.028 mole) of BBr$_3$ in 10 ml of CH$_2$Cl$_2$. After 1 5 hr, the reaction mixture was cooled to 0°, and methanol was cautiously added. After a vigorous reaction subsided, the solvents were evaporated. The residue was recrystallized from ethanol to give 1-[3-(4-hydroxyphenyl)-propyl]-2-mercaptoimidazole, 1.02 g (67%), mp 185°.

EXAMPLE 8

1-[3-(4—Hydroxyphenyl)propyl]-2-thiomethylimidazole

A solution of 1.2 g (.0046 mole) of 1-[3-(4methoxyphenyl)propyl]-2-mercaptoimidazole in 40 ml of CH$_2$Cl$_2$ was treated with a solution of 3.5 g (.014 mole) of BBr$_3$ in 10 ml of CH$_2$Cl$_2$. After 4 hours, methanol was cautiously added, the mixture was stirred for an additional 18 hours, and the solvents were evaporated. The residue was dissolved in H$_2$O, washed with ethyl acetate, neutralized with NaHCO and extracted with ethyl acetate. The extracts were dried (MgSO$_4$) and filtered and the solvent was evaporated. The residue was dissolved in 5 ml of ethanol, and treated with ethereal HCl. A crystalline product was filtered and recrystallized from ethanol, to give 1-[3-(4-hydroxyphenyl)-propyl]-2-thiomethylimidazole hydrochloride, 0.61 g (45%), mp 140–142°.

EXAMPLE 9

1-(3-Nitro-4-hydroxybenzyl)-2-mercaptoimidazole

A solution of 1-[3'-nitro-4'-methoxybenzyl]-2mercaptoimidazole (1.59 g, 6.0 moles) in 10% aqueous NaOH (200 ml) was refluxed for two hours, cooled, acidified with concentrated HCl, cooled and filtered. The crystalline product was washed with water. Recrystallization from ethanol provided 1.25 g (80%) of product as yellow prisms: mp 225–227° (dec).

EXAMPLE 10

1-(2,6-Dichloro-4-hydroxybenzyl)-2-mercaptoimidazole

A mixture of 1-[2',6'-dichloro-4'-methoxybenzyl]2-mercaptoimidazole (1 g) in concentrated aqueous hydrobromic acid (50 ml) was heated at reflux under argon for 1.25 hr, and then cooled. The product was collected by filtration. Washing with concentrated aqueous hydrobromic acid and water and drying yielded 0.64 g (60%) of product as light yellow crystals: mp 235° (dec).

EXAMPLE 11

1-(3-Trifluoromethyl-4-hydroxybenzyl)-2-mercaptoimidazole

A mixture of 1-(3'-trifluoromethyl-4'-methoxy- benzyl)-2-mercaptoimidazole (2.0 g) and pyridine hydrochloride (15 g) was melted at 210° for 30 minutes, cooled, diluted with water and extracted with ethyl acetate. The ethyl acetate extracts were treated with charcoal, dried over sodium sulfate and concentrated to give a thick oil. Addition of THF (3 ml), ether (6 ml), and hexane (15 ml) produced yellow crystals. Recrystallization from ethyl acetate/hexane yielded 0.7 g (37%) of cream colored crystals: mp 220° (dec).

EXAMPLE 12

3',5'-Dichlorobenzyl)-2-mercaptoimidazole

A mixture of 3,5-dichlorobenzaldehyde (17.5 g, 0.1 mole) and aminoacetaldehyde diethylacetal (13.3 g, 0.1 mole) was heated on a steam bath. The resulting solution was stirred at room temperature during slow addition of sodium borohydride (3 g, 0.08 mole) and the mixture was stirred overnight at room temperature. The mixture was concentrated under reduced pressure, and the residue was partitioned between ethyl acetate and water. The ethyl acetate layer was washed sequentially with water and brine, and then dried over anhydrous sodium sulfate, and concentrated under reduced pressure. The resulting oil was heated at reflux with water (100 ml), concentrated hydrochloric acid (22 ml), ethanol (41 ml), and potassium thiocyanante (10.7 g, 0.11 mole) for 2 hours. The mixture was cooled and diluted with water (250 ml), and the crude product was collected by filtration and dried. Recrystallization twice from acetic acid provided 7.3 g (30%) of the title compound as light yellow crystals: mp 209–211°.

EXAMPLE 13

1-(2',6'-Dichlorobenzyl)-2-mercaptoimidazole

Reaction of 2,6-dichlorobenzaldehyde (17.5 g, 0.1 mole) and aminoacetaldehyde diethyl acetal (13.3 g, 0.1 mole) substantially as above yielded 5.4 g (21%) of the title compound as white needles: mp 242-3° (ethanol/ether).

EXAMPLE 14

1-(2'—Chlorobenzyl)-2-mercaptoimidazole

Reaction of 2-chlorobenzaldehyde (14 g, 0.1 mole) and aminoacetaldehyde diethylacetal (13.3 g, 0.1 mole) substantially as above yielded 11.2 g (50%) of the title compound as white crystals: mp 206-7° (acetone/ethanol).

EXAMPLE 15

1-(2',5'-Dichlorobenzyl)-2-mercaptoimidazole

Reaction of 2,5-dichlorobenzaldehyde (10.25 g, 0.059 mole) and aminoacetaldehyde diethyl acetal (7.79 g, 0.059 mole) substantially as above yielded 5.2 g (34%) of the title compound as white crystals: mp 265° (dec) (propionic acid).

EXAMPLE 16

1-(4'—Chlorobenzyl)-2-mercaptoimidazole

Reaction of 4-chlorobenzaldehyde (14 g, 0.1 mole) and aminoacetaldehyde diethyl acetal (13.3 g, 0.1 mole) substantially as above yielded 8.3 g (36%) of the title compound as white crystals: mp 187-9° (acetonitrile).

EXAMPLE 17

1-(2',3'-Dichlorobenzyl)-2-mercaptoimidazole Reaction of 2,3-dichlorobenzaldehyde (8.7 g, 0.05 mole) and aminoacetaldehyde diethyl acetal (6.65 g, 0.05 mole) substantially as above yielded 3.0 g (23%) of the title compound as white crystals: mp 195–7° (ethanol).

EXAMPLE 18

1-(4'—Fluorobenzyl)-2-mercaptoimidazole Reaction of 4-fluorobenzaldehyde (12.4 g, 0.1 mole) and aminoacetaldehyde diethyl acetal (13.3 g, 0.1 mole) substantially as above yielded 13.0 g (62.5%) of the title compound as white crystals: mp 167–9° (ethanol).

EXAMPLE 19

1-(3',4'-Dichlorobenzyl)-2-mercaptoimidazole Reaction of 3,4-dichlorobenzaldehyde (17.5 g, 0.1 mole) and aminoacetaldehyde diethyl acetal (13.3 g, 0.1 mole) substantially as above yielded 10 g (39%) of the title compound as white crystals: mp 178–81° (ethanol).

EXAMPLE 20

(2',4'-Dichlorobenzyl)-2-mercaptoimidazole Reaction of 2,4-dichlorobenzaldehyde (17.5 g, 0.1 mole) and aminoacetaldehyde diethyl acetal (13.3 g, 0.1 mole) substantially as above yielded 8.5 g (33%) of the title compound as of white crystals: mp 185–7° (2-propanol).

EXAMPLE 21

1-(3'—Chlorobenzyl)-2-mercaptoimidazole Reaction of 3-chlorobenzaldehyde (14 g, 0.1 mole) and aminoacetaldehyde diethyl acetal (13.3 g, 0.1 mole) substantially as above yielded 14 g (62.5%) of the title compound as white crystals: mp 129–131° (acetonitrile).

EXAMPLE 22

(2',4',6'-Trichlorobenzyl)-2-mercaptoimidazole Reaction of 2,4,6-trichlorobenzaldehyde (20.9 g, 0.1 mole) and aminoacetaldehyde diethylacetal (13.3 g, 0.1 mole) substantially as above yielded 12 g (46%) of the title compound as white crystals: mp 240–4° (ethanol).

EXAMPLE 23

1-(3—Fluorobenzyl)-2-mercaptoimidazole Reaction of 3-fluorobenzaldehyde (24.8 g, 0.2 mole) and aminoacetaldehyde diethyl acetal (26.6 g, 0.2 mole) substantially as above yielded 28 g (67%) of the title compound as white crystals: mp 112.5–114° (2-propanol/water).

EXAMPLE 24

1-(3',5'-Difluorobenzyl)-2-mercaptoimidazole Reaction of 3,5-difluorobenzaldehyde (14.7 g, 0.104 mole) and aminoacetaldehyde dimethyl acetal (10.8 g, 0.104 mole) substantially as above yielded 10.0 g (43%) of the title compound as white crystals: mp 140–141° (ethyl acetate/hexane).

EXAMPLE 25

1-[3-(3',5'-Difluorophenyl)propyl]-2-mercaptoimidazole 3,5-Difluorobenzaldehyde (5.5 g, 0.039 mole), malonic acid (6.06 g, 0.058 mole), pyridine (2.1 ml) and piperidine (0.105 ml) were heated on a steam bath for 2 hours and then at 155° for 1 hour. The reaction mixture was poured into cold 3N aqueous hydrochloric acid, and then filtered. Recrystallization from ethanol provided 4.7 g (66%) of 3,5-difluorocinnamic acid as buff needles: mp 199–201°.

3-5-Difluorocinnamic acid (4.6 g, 0.025 mole) was dissolved in tetrahydrofuran (50 ml) and added to a slurry of 0.75 g palladium/carbon in ethyl acetate. The mixture was shaken under 50 psi (.34 MPa) hydrogen for 5 hours and then was filtered and concentrated to provide 4.5 g (97%) of 3-(3',5'-difluorophenyl)-propanoic acid as colorless crystals: mp 56° (methanol).

A solution of 3-(3'5'-difluorophenyl) propanoic acid (4.4 g, 0.024 mole) N,N-dimethylformamide (one drop) and thionyl chloride (15 ml) was heated at 60° for 3 hours. Excess thionyl chloride was removed by distillation at reduced pressure. Distillation (Kugelrohr) at reduced pressure (about 0.25 mm [33 Pa]) yielded 4.1 g (85%) of 3-(3',5'-difluorophenyl)propionyl chloride as an oil.

A solution of 3-(3',5'-difluorophenyl)propionyl chloride (4 g, 0.0196 mole) in methylene chloride (40 ml) was slowly added to a 0° solution of amino acetaldehyde dimethyl acetal (4.3 g, 0.0412 mole) in methylene chloride (100 ml) at a rate such that the temperature did not exceed 20°. The reaction mixture was stirred for 1 hour. Then it was poured into water and the layers were separated. The organic layer was washed with 5% aqueous sodium carbonate, 0.05% aqueous hydrogen chloride, and water and then was dried over sodium sulfate and concentrated to yield 5.5 g (103%) of 3-(3',5'difluorophenyl))propanamide N-acetaldehyde dimethyl acetal as an oil.

A solution of 3-(3',5'-difluorophenyl)propanamide N-acetaldehyde dimethyl acetal (5.3 g, 0.0194 mole) in diethyl ether (100 ml) was slowly added to a slurry of lithium aluminum hydride (4.4 g, 0.116 mole) in diethyl ether (200 ml). The reaction mixture was stirred at ambient temperature (20–25°) for 18 hours. Then water (4.5 ml) was carefully added, followed by 10% aqueous sodium hydroxide (7 ml) and water (11 ml). The mixture was filtered and the filtrate was dried over sodium sulfate and concentrated to yield 4.4 g (88%) of (3',5'-difluorophenyl)propanamine N-acetaldehyde dimethyl acetal as colorless oil.

A solution of 3-(3',5'-difluorophenyl)propanamine N-acetaldehyde dimethyl acetal (4.3 g, 0.0166 mole) and potassium thiocyanate (1.6 g, 0.0166 mol) in ethanol (12 ml), water (20 ml), and concentrated hydrochloric acid (4 ml) was refluxed for 1 hour and then cooled and a large volume of water was added. The product was filtered and recrystallized to yield 2.2 g (55%) of 1-[3-(3',5'difluorophenyl)propyl]2-mercaptoimidazole as white needles: mp 131–132° (ethanol).

EXAMPLE 26

3-(3', 5'-Dichlorophenyl)propyl-2-mercaptoimidazole

Reaction of 3,5-dichlorobenzaldehyde (26.9 g, 0.154 mole), malonic acid (24.1 g, 0.232 mole), pyridine (8 ml) and piperidine (0.4 ml) substantially as above yielded 22.9 g (69%) of 3,5-dichlorocinnamic acid as white needles: mp 169–170° (ethanol).

Reaction of 3,5-dichlorocinnamic acid (22.9 g, 0.106 mol) and 3 g palladium/carbon substantially as above yielded 23 g (99%) of 3-(3',5'-dichlorophenyl)propanoic acid as an oil.

A one molar solution of borane in tetrahydrofuran (233 ml) was added dropwise to a cooled (0°) solution of 3-(3',5'-dichlorophenyl)propanoic acid (23 g, 0.106 mole) in distilled tetrahydrofuran (200 ml). The reaction was stirred at room temperature for 2 hours. Then methanol was added and the solution was concentrated to yield 21.2 g (98%) of 1-[3-(3',5'-dichlorophenyl)]-propanol as a clear oil.

Dimethyl sulfoxide (6.75 g, 0.083 mole) in dry methylene chloride (15 ml) was added dropwise to a solution of oxalylchloride (6.2 g, 0.049 mole) in dry methylene chloride (15 ml) at −78°. The reaction mixture was stirred for 2 minutes. Then 1-[3-(3',5'dichlorophenyl)]- propanol (5 g, 0.0245 mole) in dry methylene chloride (20 ml) was slowly added, keeping the temperature below −60°. After stirring for 15 minutes at −70°, triethylamine (16 g, 0.160 mol) was added dropwise. The reaction mixture was stirred for an additional 5 minutes at −60° and then was warmed to room temperature and diluted with water. The organic layer was separated, washed with 3N hydrogen chloride and then with brine, and was dried over sodium sulfate. The solution was concentrated to give 5.0 g (100%) of 3-(3′,5′dichlorophenyl) propionaldehyde as a yellow oil.

Amino acetaldehyde dimethyl acetal (2.1 g, 0.0197 mole) was added with stirring to a solution of 3—(3′,5′-dichlorophenyl)propionaldehyde (5 g, 0.025 mole) in hexane (10 ml). After stirring for 1 hour at room temperature, sodium borohydride (7.3 g, 0.193 mole) in ethanol (25 ml) was added. The reaction mixture was stirred for 18 hours and then was diluted with water and concentrated. The residue was taken up in ethyl acetate, washed with water, dried over sodium sulfate and concentrated to yield 6.8 g (93%) of 3—(3′,5′- dichlorphenyl)propanimide N-acetaldehyde dimethyl acetal as a yellow oil.

A solution of 3-(3′,5′-dichlorophenyl)propanamide N-acetaldehyde dimethyl acetal and potassium thiocynate (2.2 g, 0.0223 mole) in ethanol (20 ml), water (30 ml), and concentrated hydrochloric acid was refluxed for 1 hour. The reaction mixture was cooled and diluted with water. After standing for 3 hours, the crude product solidified and was filtered. Chromatography on silica, eluting with 0.5 to 1% methanol in methylene chloride, provided 2.0 g (31%) of 3—(3′,5′-dichlorophenyl)propyl-2mercaptoimidazole as white crystals: mp 98–99° (ethanol).

EXAMPLES 27–58

The compounds listed in Table IV, below, are prepared substantially by the procedures illustrated in the preceding Examples except that equivalent molar amounts of appropriate starting compounds and of other reactants and reagents are used.

The compounds in which X and/or Y is —OH are prepared from corresponding methoxy-substituted compounds which are deprotected as illustrated above.

In particular, the compounds of Examples 29, 32, 36 and 38 are prepared from mercaptoimidazoles as follows:

| Example | Mercaptoimidazoles |
|---|---|
| 30 | 1-[3-(3-carboxamido-4-methoxyphenyl)-propyl]-2-mercaptoimidazole |
| 33 | 1-[2-(2,3-di(trifluoromethyl)-4-methoxyphenylethyl]-2-mercapto-imidazole |
| 36 | 1-[2-(3-cyano-4-methoxyphenyl)-ethyl]-2-mercaptoimidazole |
| 38 | 1-[3-(2-methoxy-4-carbomethoxyphenyl)-propyl]-2-mercaptoimidazole |

The compound of Example 33, in which R is —$(CH_2)_3 CH_3$ is prepared by allowing the deprotection with $BBr_3$ in butanol to proceed to formation of butyl bromide The butyl bromide alkylates the mercapto moiety as in Example 6, above.

TABLE IV

| EXAMPLE | n | X | Y | R |
|---|---|---|---|---|
| 27 | 0 | 3-$CH_3$,5-$CH_3$ | $CH_3$ | H |
| 28 | 3 | 2-CN | $CH_2OH$ | H |
| 29 | 1 | 3-$SO_2NH_2$ | H | H |
| 30 | 3 | 3-$CONH_2$ | OH | H |
| 31 | 4 | 2-CHO | H | H |
| 32 | 4 | 2-$CH_2OH$,3-$CH_3$ | $CF_3$ | H |
| 33 | 2 | 2-$CF_3$,3-$CF_3$ | OH | $(CH_2)_3CH_3$ |
| 34 | 1 | 3-$SO_2CF_3$ | H | H |
| 35 | 1 | 3-$CO_2(CH_2)_3CH_3$ | H | H |
| 36 | 2 | 3-CN | OH | H |
| 37 | 4 | H | $SO_2NH_2$ | H |
| 38 | 3 | 2-OH | $CO_2H$ | H |
| 39 | 0 | H | $CONH_2$ | H |
| 40 | 1 | 3-$OCH_3$ | $SO_2CH_2CH_3$ | H |
| 41 | 1 | H | $SO_2(CF_2)_3CF_3$ | H |
| 42 | 1 | 3-$(CF_2)_3CF_3$ | $CO_2CH_3$ | H |
| 43 | 1 | 2,3,5,6-$F_4$ | F | |
| 44 | 3 | 2,3,5,6-$F_4$ | F | H |
| 45 | 1 | 2,3-$F_2$ | H | H |
| 46 | 1 | 2-F | F | H |
| 47 | 1 | 2,5-$F_2$ | H | H |
| 48 | 1 | 2,6-$F_2$ | H | H |
| 49 | 1 | 3-F | F | H |
| 50 | 1 | 3,5-$F_2$ | F | H |
| 51 | 4 | 3,5-$F_2$ | H | H |
| 52 | 3 | 3-Cl,5-F | H | H |
| 53 | 1 | 3-Cl,5-F | H | H |
| 54 | 2 | 3,5-$F_2$ | H | H |
| 55 | 0 | 3,5-$F_2$ | H | H |
| 56 | 1 | 3-Cl,5-F | F | H |
| 57 | 1 | 3-Br,5-F | H | H |
| 58 | 1 | 3-I,5-F | H | H |

EXAMPLES 59–68

The compounds shown in V, below, are prepared by alkylating corresponding mercaptoimidazoles of the invention with methyl iodide in methanol by known techniques. Other alkyl halides, for example, methyl bromide, methyl chloride and butyl iodide, are substituted for methyl iodide in an appropriate solvent. The salts are neutralized to the free base with, for example, sodium hydroxide or sodium carbonate, and can be converted to another pharmacologically acceptable acid addition salt.

TABLE V

| EXAMPLE | n | X | Compound Y | R |
|---|---|---|---|---|
| 59 | 1 | 3-$(CH_2)_3CH_3$ | F | $CH_3$ |
| 60 | 1 | 3-$SO_2CH_3$ | $(CH_2)_3CH_3$ | $CH_3$ |
| 61 | 4 | 2-CHO | CHO | $CH_3$ |
| 62 | 1 | 3,5-$F_2$ | H | $CH_3$ |
| 63 | 1 | 2,4-$F_2$ | H | $CH_3$ |
| 64 | 3 | 3,5-$F_2$ | H | $CH_3$ |
| 65 | 4 | 3,5-$F_2$ | H | $CH_3$ |
| 66 | 3 | 3,5-$F_2$ | H | $CH_2CH_3$ |
| 67 | 1 | 3,5-$F_2$ | H | $(CH_2)_3CH$ |
| 68 | 1 | 3,5-$F_2$ | H | $CH_2CH_3$ |

EXAMPLE 69

The ingredients in Table VI, below, are screened, mixed and filled into a hard gelatin capsule.

TABLE VI

| Ingredients | Amounts |
|---|---|
| 1-[3-(4-hydroxyphenyl)-propyl]-2-mercaptoimidazole | 50 mg |
| magnesium stearate | 5 mg |
| lactose | 75 mg |

EXAMPLE 70

The sucrose, calcium sulfate dihydrate and imidazole shown in Table VII, below, are mixed and granulated with a 10% gelatin solution. The wet granules are screened, dried, mixed with the starch, talc and stearic acid, screened and compressed into a tablet.

TABLE VII

| Ingredients | Amounts |
| --- | --- |
| 1-[2',6'-dichloro-4'-hydroxybenzyl]-2-mercaptoimidazole | 100 mg |
| calcium sulfate dihydrate | 150 mg |
| sucrose | 20 mg |
| starch | 10 mg |
| talc | 5 mg |
| stearic acid | 3 mg |

EXAMPLE 71

1-3-(4—Hydroxyphenyl)propyl]-2-thiomethylimidazole 75 mg, is dissolved in z5 ml of normal saline to prepare an injectable preparation.

While the preferred embodiments of the invention are illustrated by the above, it is to be understood that the invention is not limited to the precise constructions herein disclosed and that the right to all modifications coming within the scope of the following claims is reserved.

What is claimed is:

1. A compound having the formula:

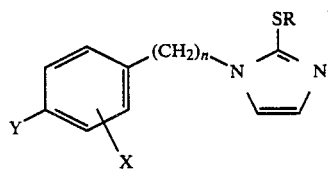

wherein:
X is 1-halogens or up to two substituents selected from —H, —OH, $C_{1-4}$ alkyl, —CN, —NO$_2$, —SO$_2$NH$_2$, —CO$_2$H, —COHN$_2$, —CHO, —CH$_2$OH, —CF$_3$, $C_{1-4}$ alkoxy, —SO$_2$C$_{1-4}$ alkyl —SO$_2$C$_{1-4}$ flurooalkyl, or —CO$_2$C$_{1-4}$ alkyl;
Y is —H, —OH, $C_{1-4}$ alkoxy, halogen, $C_{1-4}$ alkyl, —CN, —NO$_2$, —SO$_2$NH$_2$, —CO$_2$H, —CONH$_2$, —CHO, —CH$_2$OH, —CF$_3$, —SO$_2$C$_{1-4}$ aklyl, —SO$_2$C$_{1-4}$ fluoroalkyl, or —CO$_2$C$_{1-4}$ alkyl;
R is —H or $C_{1-4}$ alkyl; and,
n is 1-4
or a hydrate, or, when R is $C_{1-4}$ aklyl, a pharmaceutically acceptable acid addition salt thereof, provided that when n is 1-3, at least one of Y and X is not —H.

2. The compound of claim 1 wherein Y is —OH.

3. The compound of claim 2 wherein R is —H, n is 1 or 3 and X is —H, —OH or halogen.

4. The compound of cliam 3 wherein X is —H, —OH, 3,5-dichloro, 3,5difluoro, or 3-fluror.

5. The compound of claim 4 wherein X is 3,5-difluoro and n is 1.

6. The compound of claim 1 wherein Y is —H.

7. The compound of claim 6 wherein R is —H, n is 1 or 3 and X is —OH or halogen.

8. The compound of claim 7 wherein X is —OH, 3,5-dichloro, 3,5-difluoro, 3-chloro or 3-fluoro.

9. The compound of claim 8 wherein X is 3,5-difluoro and n is 1.

10. The compound of claim 1 wherein:
X is —H, Y is —OH, R is —H, and n is 0-4;
X is 3—OH, 3—Cl, 3—CH3, 3-Br, 3—F, 3-N02, —CF3, 3,5-dichloro, 3,5-difluoro, 2,6-dichloro or 2,3,5,6-tetrafluoro, Y is —OH, R is —H and n is 1;
X is —H, Y is —OH, R is —CH$_3$ and n is 3;
X is —H, Y is —F, R is —H and n is 1;
X is 3—Cl, Y is —Cl, R is —H and n is 1;
X is 2,6-dichloro, 2—Cl, 2,5-dichloro, 2,3-dichloro, 3—Cl, 3,5-dichloro, 3—F, 3,5-difluoro, Y is —H, R is —H and n is 1;
X is —H, 3—Cl, 2—Cl, 2,6-dichloro, Y is —Cl, R is —H and n is 1;
X is 3,5-dichloro or 3,5-difluoro, Y is —H, R is —H and n is 3; or
X is 3—OH, 2—OH, 2—OCH3, 3—OCH3 or —H, Y is —H, R is —H and n is 1

11. The compound of claim 1 wherein Y is —OCH3

12. The compound of claim 11 wherein X is 3—F, R is H, and n is 1, or X is 3,5—F2, R is H, and n is 1.

13. A pharmaceutical composition having DBH inhibiting activity in mammals comprising an amount effective to produce said inhibition of a compound having the formula:

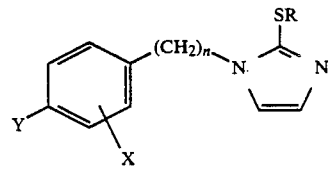

wherein:
X is 1-4 halogens or upt to two substituents selected from —h, —oh, $C_{1-4}$ alkyl, —CN, —NO$_2$, —SO$_2$NH$_2$, —CO$_2$H, —CONH$_2$, —CHO, —CH$_2$OH, —CF$_3$, $C_{1-4}$ alkoxy, —SO$_2$C$_{1-4}$ alkyl, —SO$_2$C$_{1-4}$ fluroalkyl, or —CO$_2$C$_{1-4}$ alkyl;
Y is ——H, —OH, $C_{1-4}$ alkoxy, halogen, $C_{1-4}$ alkyl, —CN, —NO$_2$, —SO$_2$NH$_2$, —CO$_2$H, —COHN$_2$, —CHO, —CH$_2$OH, —CF$_3$, —SO$_2$C$_{1-4}$ alkyl, —SO$_2$C$_{1-4}$ fluroalkyl, or —CO$_2$C$_{1-4}$ alkyl;
R is —H or $C_{1-4}$ alkyl; and
n is 0-0
or a hydrate or, when R is $C_{1-4}$ alkyl,. a pharmaceutically acceptable acid additon salt thereof, provided that when n is O, Y is —OH, or $C_{1-4}$ alkoxy, and a suitable carrier.

14. The pharmaceutical composition of claim 13 wherein Y is —OH.

15. The pharmaceutical composition of claim 14 wherin R is —H, n is 1 or 3 and X is —H, —OH or halogen.

16. The pharmaceutical composition of claim 15 wherin X is —H, —OH, 3,5- dichloro, 3,5-difluoro, 3-chloro or 3-fluoro.

17. The pharmaceutical composiiton of claim 16 wherin X is 3,5-difluoro and n is 1.

18. The pharmaceutical composition of claim 13 wherein Y is —H.

19. The pharmaceutical composition of claim 18 wherein R is —H, n is 1 or 3 and X is —OH or halogen.

20. The pharmaceutical composition of claim 19 wherein X is —OH, 3,5-dichloro, 3,5-difluoro, 3-chloro or 3-fluoro.

21. The pharmaceutical composition of claim 20 wherein X is 3,5-difluoro and n is 1.

22. The pharmaceutical composition of claim 13 wherein:
X is —H, Y is —OH, R is —H, and n is 0–4;
X is 3—OH, 3—Cl, 3—CH$_3$, 3-Br, 3—F, 3-N0$_2$, —CF$_3$, 3,5-dichloro, 3,5-difluoro, 2,6-dichloro or 2,3,5,6-tetrafluoro, Y is —OH, R is —H and n is 1;
X is —H, Y is —OH, R is —CH3 and n is 3;
X is H, Y is —F, R is —H and n is 1;
X is 3—Cl, Y is —Cl, R is —H and n is 1;
X is 2,6-dichloro, 2—Cl, 2,5-dichloro, 2,3-dichloro, 3—Cl, 3,5-dichloro, 3—F, 3,5-difuloro, Y is —H, R is —H and n is 1;
X is —H, 3—Cl, 2—Cl, 2,6-dichloro, Y is —Cl, R, is —H and n is 1;
X is 3,5-dichloro or 3,5-difluoro, Y is —H, R is —H and n is 3; or
X is 3—OH, 2—OH, 2—OCH$_3$, 3—OCH3 or —H, Y is —H, R is —H and n is 1.

23. The pharmaceutical composition of claim 13 wherein Y is —OCH$_3$.

24. The pharmaceutical composition of claim 23 wherein X is 3—F, R is H, and n is 1, or X is 3,5—F2, R is H, and n is 1.

25. A method of inhibiting DBH activity in mannals which comprises adminstering internally to a subject an effective amount of a compound having the formula:

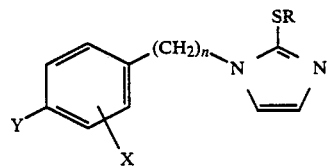

wherein:
X is 1-halogens or upt to two substituents selected from —h, —OH, C$_{1-4}$ alkyl, —CN, —NO$_2$ —SO$_2$NH$_2$, —CO$_2$H, —COHN$_2$, —CHO, —CH$_2$OH, —CF$_3$, C$_{1-4}$ alkoxy, —SO$_2$C$_{1-4}$ alkyl, —SO$_2$C$_{1-4}$ flurooalkyl, or —CO$_2$C$_{1-4}$ alkyl;
Y is —H, —OHm, C$_{1-4}$ alkoxy, halogen, C$_{1-4}$ alkyl, —C,N —NO$_2$, —SO$_2$NH$_2$, —CO$_2$H, —CONH$_2$, —CHO, —CH$_2$OH, —CF$_3$, —SO$_2$C$_{1-4}$ alkyl, —SO$_2$C$_{1-4}$ fluoroalkyl, or —CO$_2$C$_{1-4}$ alkyl;
R is —H or C$_{1-4}$ alkyl; and
n is 0–4,
or a hydrate or, when R is C$_{1-4}$ alkyl, a pharmaceutically acceptable acid addition salt thereof.

26. The method of claim 25 wherien Y is —OH.

27. The method of claim 26 wherein R is —H, n is 1 or 3 and X is —H, —OH or halogen.

28. The method of claim 27 wherin X is —H, —OH, 3,5-dichloro, 3,5-difluoro, 3-chloro or 3-fluoro.

29. The method of claim 28 wherein X is 3,5-difluoro and n is 1.

30. The method of claim 25 wherein Y is —H.

31. The method of claim 30 wherein R is —H, n is or 3 and X is —OH or halogen.

32. The method of claim 31 wherein X is —OH, 3,5-dichloro, 3,5-difluoro, 3-chloro or 3-fluoro.

33. The method of claim 32 wherein X is 3,5-difluoro and n is 1.

34. The method of claim 25 wherein:
X is —H, Y is —OH, R is —H and n is 0–4;
X is 3—OH, 3—Cl, 3—CH3, 3-Br, 3—F, 3-N02, —CF3, 3,5-dichloro, 3,5-difluoro, 2,6-dichloro or 2,3,5,6-tetrafluoro, Y is —OH, R is —H and n is 1;
X is —H, Y is —OH, R is —CH3 and n is 3;
X is H, Y is —F, R is —H and n is 1;
X is 3—Cl, Y is —Cl, R is —H and n is 1;
X is 2,6-dichloro, 2—Cl, 2,5-dichloro, 2,3-dichloro, 3—Cl, 3,5-dichloro, 2,4,6-trichloro, 3—F, 3,5-difluoro, Y is —H, R is —H and n is 1;
X is —H, 3—Cl, 2—Cl, 2,6-dichloro, Y is —Cl, R is —H and n is 1;
X is 3,5-dichloro or 3,5-difluoro, Y is —H, R is —H and n is 3;
X is 3—OH, 2—OH, 2—OCH$_3$, 3—OCH$_3$ or —H, Y is —H, R is —H and n is 1; or
X is —H, Y is —H, R is —H and n is 0.

35. The method of claim 25 wherein Y is OCH$_3$.

36. The method of claim 36 wherein X is 3—F, R is H, and n is 1, or X is 3,5—F2, R is H, and n is 1.

37. A compound having the formula:

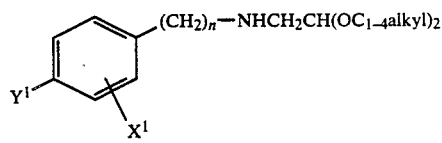

wherein
Y$^1$ is —H, halogen, C$_{1-4}$ alkyl, —CN, —NO$_2$, —SO$_2$NH$_2$, —CO$_2$H, —CONH$_2$, —CHO, —CH$_2$OH, —CF$_3$, C$_{1-4}$ alkoxy, —SO$_2$C$_{1-4}$ alkyl, —SO$_2$C$_{1-4}$ flurooalkyl, or —CO$_2$C$_{1-4}$ alkyl; and
X$^1$ is 1-4 halogens or up to two substituents selected from —H, C$_{1-4}$ alkyl, —CN, —NO$_2$, —SO$_2$NH$_2$, —CO$_2$H, —CONH$_2$, —CHO, —CH$_2$OH, —CF$_3$, C$_{1-4}$ alkoxy, —SO$_2$C$_{1-4}$ alkyl, —SO$_2$C$_{1-4}$ fluoroalkyl, or —CO$_2$C$_{1-4}$ alkyl; and
n is 0–4, provided that when n is 0 Y$^1$ is OCH$_3$ and when n is 1–3, at least one of Y$^1$ and X$^1$ is not —H.

38. The compound of claim 37 wherin n is 1–4.

39. A compound having the formula:

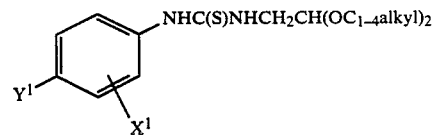

wherein:
Y$^1$ is C$_{1-4}$ alkoxy;
X$^1$ is 1-4 halogens or upt to two substituents sleected from —H, C$_{1-4}$ alkyl, —CN, —NO$_2$, —SO$_2$NH$_2$, —CO$_2$H, —CONH$_2$, —CHO, —CH$_2$OH, —CF$_3$, C$_{1-4}$ alkoxy, —SO$_2$C$_{1-4}$ alkyl, —SO$_2$C$_{1-4}$ fluroalkyl, or —CO$_2$C$_{1-4}$ alkyl.

40. The compound of claim 1 wherein:
X is 3,5-difluoro, Y is H, R is CH$_3$, and n is 1.

41. A pharmaceutical composoition of claim 13 wherein:
X is 3,5-difluoro, Y is H, R is CH$_3$, and n is 1.

42. A method of claim 25 wherin:
X is 3,5-difluoro, Y is H, R is CH$_3$, and n is 1.

43. A method of treatmetn to reduce blood pressure in a subject that comprises administering internally to a subject an effective amount of a compound having the formula:

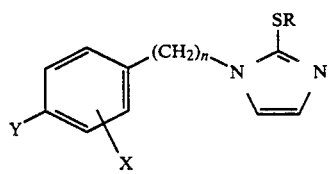

wherein:

X is 1–4 halogens or upt to two substituents selected from —H, —OH, $C_{1-4}$ alkyl, —CN, —NO$_2$, —SO$_2$NH$_2$, —CO$_2$H, —CONH$_2$, —CHO, —CH$_2$OH, —CF$_3$, $C_{1-4}$ alkoxy, —SO$_2C_{1-4}$ alkyl, —SO$_2C_{1-4}$ fluoroalkyl, or —CO$_2C_{1-4}$ alkyl;

Y is —H, —OH, $C_{1-4}$ alkoxy, halogen, $C_{1-4}$ alkyl, —cn —NO$_2$, —SO$_2$NH$_2$, —CO$_2$H, —CONH$_2$, —CHO, —CH$_2$, —CF$_3$, —SO$_2C_{1-4}$ alkyl, —SO$_2C_{1-4}$ fluoroalkyl, or —CO$_2C_{1-4}$ alkyl;

R is —H or $C_{1-4}$ alkyl; and n is 0–4, or a hydrate or, when R is $C_{1-4}$ alkyl, a pharmaceutically acceptable acid addition salt thereof.

44. A method of claim 43 wherien the compound is 1-(3,5-difluorobenzyl)-2mercaptoimidazole), 1-(3-fluoro-4-methoxybenzyl)-2-mercaptoimidazole, or 1-(3,5-difluorobenzyl)-2-methylthioimidazole.

* * * * *